US008107695B2

(12) United States Patent
Wollenweber

(10) Patent No.: US 8,107,695 B2
(45) Date of Patent: Jan. 31, 2012

(54) METHODS AND SYSTEMS FOR ASSESSING PATIENT MOVEMENT IN DIAGNOSTIC IMAGING

(75) Inventor: Scott David Wollenweber, Waukesha, WI (US)

(73) Assignee: General Electric Company, Schenectady, NY (US)

(*) Notice: Subject to any disclaimer, the term of this patent is extended or adjusted under 35 U.S.C. 154(b) by 1061 days.

(21) Appl. No.: 11/823,231

(22) Filed: Jun. 27, 2007

(65) Prior Publication Data

US 2009/0003655 A1 Jan. 1, 2009

(51) Int. Cl.
*G06K 9/00* (2006.01)
*G06K 9/32* (2006.01)

(52) U.S. Cl. ........ 382/128; 382/107; 382/298; 600/415; 600/595

(58) Field of Classification Search .................. 382/107, 382/128, 131, 298; 600/407, 415, 527, 595; 128/922
See application file for complete search history.

(56) References Cited

U.S. PATENT DOCUMENTS

| | | | | |
|---|---|---|---|---|
| 4,912,770 A * | 3/1990 | Seto et al. | ...... | 382/107 |
| 5,272,343 A * | 12/1993 | Stearns | ...... | 250/363.03 |
| 5,291,402 A * | 3/1994 | Pfoh | ...... | 378/13 |
| 5,377,250 A * | 12/1994 | Hu | ...... | 378/15 |
| 5,430,738 A * | 7/1995 | Tsuda | ...... | 714/748 |
| 5,703,965 A * | 12/1997 | Fu et al. | ...... | 382/232 |
| 6,408,107 B1 * | 6/2002 | Miller et al. | ...... | 382/294 |
| 6,594,524 B2 * | 7/2003 | Esteller et al. | ...... | 607/45 |
| 6,819,790 B2 * | 11/2004 | Suzuki et al. | ...... | 382/156 |
| 6,870,898 B1 * | 3/2005 | von der Haar | ...... | 378/97 |
| 6,885,772 B2 * | 4/2005 | DeLong | ...... | 382/224 |
| 7,066,886 B2 * | 6/2006 | Song et al. | ...... | 600/443 |
| 7,146,218 B2 * | 12/2006 | Esteller et al. | ...... | 607/45 |
| 7,149,579 B1 * | 12/2006 | Koh et al. | ...... | 607/19 |
| 7,149,584 B1 * | 12/2006 | Koh et al. | ...... | 607/60 |
| 7,155,047 B2 * | 12/2006 | Wollenweber | ...... | 382/131 |
| 7,460,733 B2 * | 12/2008 | Xiao et al. | ...... | 382/294 |
| 7,463,922 B1 * | 12/2008 | Snyder et al. | ...... | 607/5 |
| 7,634,137 B2 * | 12/2009 | Simard et al. | ...... | 382/190 |
| 7,650,022 B2 * | 1/2010 | Kreang-Arekul et al. | .... | 382/128 |
| 7,715,607 B2 * | 5/2010 | Hu et al. | ...... | 382/131 |
| 7,720,519 B2 * | 5/2010 | Ruohonen | ...... | 600/411 |
| 2002/0039434 A1 * | 4/2002 | Levin et al. | ...... | 382/128 |
| 2002/0161798 A1 * | 10/2002 | Kanda et al. | ...... | 707/501.1 |
| 2003/0026469 A1 * | 2/2003 | Kreang-Arekul et al. | .... | 382/132 |
| 2003/0200655 A1 * | 10/2003 | Vafi et al. | ...... | 29/854 |
| 2005/0129299 A1 * | 6/2005 | Kreang-Arekul et al. | .... | 382/132 |

(Continued)

OTHER PUBLICATIONS

Watabe et al. "Performance of List Mode Data Acquisition with ECAT Exact HR Positron Emission Scanner" IEEE (2003) pp. 970-973.*

(Continued)

*Primary Examiner* — Jason M Repko
*Assistant Examiner* — Mia M Thomas
(74) *Attorney, Agent, or Firm* — Dean D. Small; The Small Patent Law Group

(57) ABSTRACT

Methods and systems for automatically detecting gross patient motion using a diagnostic medical imaging system are provided. The method provides for acquiring a plurality of frames of image data, positioning a first time window and a second time window over overlapping frames of image data, calculating a statistical correlation value based on the first time window and the second time window, and comparing a first derivative of the statistical correlation value to a threshold value to determine patient motion.

23 Claims, 5 Drawing Sheets

U.S. PATENT DOCUMENTS

| | | | | |
|---|---|---|---|---|
| 2005/0288568 A1* | 12/2005 | Pan | | 600/407 |
| 2006/0215895 A1* | 9/2006 | Ando | | 382/128 |
| 2006/0285753 A1* | 12/2006 | Yamasaki | | 382/209 |
| 2007/0253599 A1* | 11/2007 | White et al. | | 382/107 |
| 2008/0021731 A1* | 1/2008 | Rodgers | | 705/2 |
| 2009/0041305 A1* | 2/2009 | Luo et al. | | 382/107 |
| 2009/0129642 A1* | 5/2009 | Matsumoto | | 382/128 |
| 2009/0149741 A1* | 6/2009 | Heigl | | 600/424 |
| 2009/0313495 A1* | 12/2009 | Krishnan et al. | | 713/600 |
| 2010/0061596 A1* | 3/2010 | Mostafavi et al. | | 382/107 |
| 2010/0063419 A1* | 3/2010 | Mostafavi et al. | | 600/587 |
| 2010/0128953 A1* | 5/2010 | Ostrovsky-Berman | | 382/131 |

OTHER PUBLICATIONS

Pratt et al. "Correlation Techniques of Image Registration" IEEE Transactions on Aerospace and Electronic Systems vol. AES-10, No. 3, May 1974, pp. 353-358.*

Slart et al. "Attentuation corrected gated SPECT for the assessment of left ventricular ejection fraction and volumes" Annual Nucl Med (2008) 22:171-176.*

Wollenweber et al. "Quantitative Analysis of PET Reconstruction Techniques over a wide Activity Range with 2D and 3D Acquisition Modes" 2006 IEEE Nuclear Science Symp. Conference Record pp. 1-3.*

\* cited by examiner

METHODS AND SYSTEMS FOR ASSESSING PATIENT MOVEMENT IN DIAGNOSTIC IMAGING

BACKGROUND OF THE INVENTION

This invention relates generally to imaging systems, and more particularly, to methods and systems for assessing gross patient movement in diagnostic imaging, especially in a PET-CT imaging.

Patient motion during a positron emission tomography (PET)-computed tomography (CT) scan may be undetected and may affect the diagnostic quality of a PET-CT scan. The motion may be both voluntary (e.g., head turn, hand movement, speaking and the like) or involuntary (e.g., breathing). Typically, a technologist may not be able to constantly monitor a patient to ensure the patient remains motionless for the period of time required for a PET scan (e.g., 20-30 minutes or more). In addition, some patients have certain physical conditions causing them difficulty in remaining still or remaining in a particular position for any length of time (e.g., pain resulting from being placed in one position for any length of time, involuntary movements from a disease such as Parkinson's disease, or, for instance, any type of kinesis, and the like). In addition, some positions, which may be advantageous for scanning, may be difficult for the patient to maintain for long durations (e.g., arms above the head).

Once motion is detected, a technologist may decide to re-scan the patient, re-prescribe a CT attenuation scan to apply to the post-motion patient position, or ensure the patient is comfortable for the remainder of the scan session, among other actions. Correcting for motion during a scan takes time and resources. Any motion caused by the patient moving during a scan decreases the quality of the images. For instance, any motion may cause the images to be blurred. Therefore, being able to monitor when a patient moves during the scan is desirable in order to improve the diagnostic quality of a PET-CT scan and reduce image time by decreasing the need for re-scans, and the like.

What is needed is method and system to automatically assess gross patient motion, such as movement of the arm position during scanning, while a patient is undergoing a scan and a radioactive tracer remains in situ. Further, the ability to detect whether a patient has moved during a scan that allows a quality of data to be addressed in real-time as well as allow for a post-scan quality assurance is needed.

BRIEF DESCRIPTION OF THE INVENTION

In one embodiment a method for automatically detecting gross patient motion using a diagnostic medical imaging system is provided. The method provides for acquiring a plurality of spatial and temporal frames of image data, positioning a first time window and a second time window over data in overlapping image frames, calculating a statistical correlation value based on the first time window and the second time window, and comparing a first derivative of the statistical correlation value to a threshold value to determine a correlation change that may indicate patient motion.

Alternatively, in another embodiment, a diagnostic medical imaging system is provided. The system includes a scanner to acquire frames of image data from a patient, a processor, and a display to output a graph of gross patient motion. The processor is configured to position a first time window and a second time window over data from overlapping spatial frames, calculate a statistical correlation value based on the first time window and the second time window, and compare a first derivative of the statistical correlation value to a threshold value.

Optionally, in another embodiment, a computer program embodied on a computer readable medium for controlling a diagnostic medical imaging system is provided. The imaging system includes a scanner to acquire frames of image data from a patient and a processor. The program includes a code segment that instructs the processor to acquire Positron Emission Tomography (PET) image data from an object. The computer program further instructs the processor to position a first time window and a second time window over overlapping frames of the image data, to calculate a statistical correlation value based on the first time window and the second time window, to compare a first derivative of the statistical correlation value to a threshold value, and to display a graph representing an indicator of the gross motion of the patient.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

Figure 1:
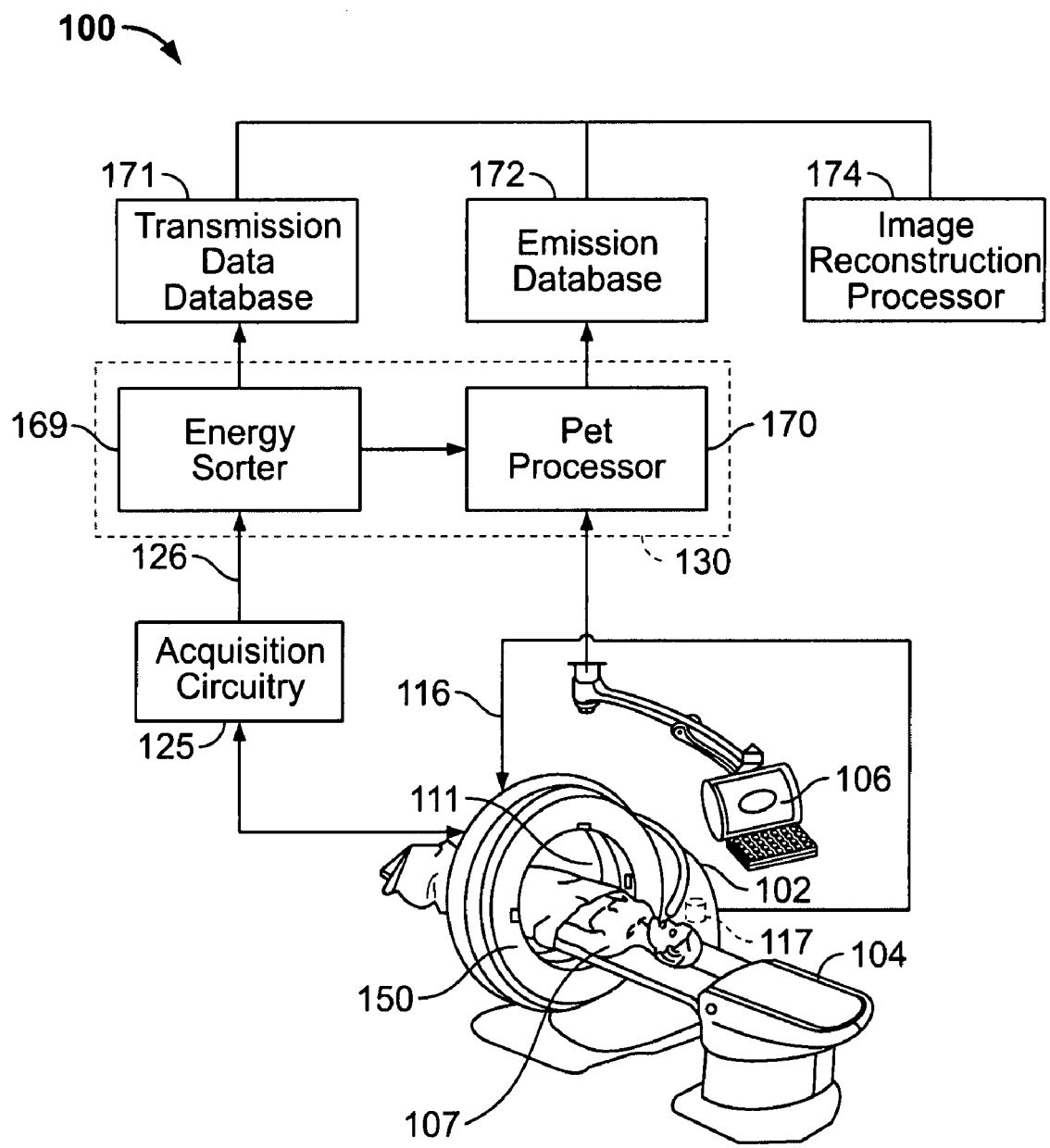
FIG. 1 is a diagram illustrating a dual PET/CT imaging system formed in accordance with an embodiment of the present invention.

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

In this document, the terms "a" or "an" are used, to include one or more than one. In this document, the term "or" is used to refer to a nonexclusive or, unless otherwise indicated. In addition, as used herein, the phrase "pixel" also includes embodiments of the present invention where the data is represented by a "voxel." Thus, both the terms "pixel" and "voxel" may be used interchangeably throughout this document.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

The systems and methods are generally directed toward multi-modal medical diagnostic imaging systems capable of scanning using different modalities, such as, for example, but not limited to, Positron Emission Tomography (PET) and Computed Tomography (CT). The term "multi-modal" refers to systems that perform scans in different modalities, for example, CT and PET. It is contemplated that the benefits of systems and methods for diagnostic imaging (e.g., MRI, SPECT, and the like) analyzing an abnormality of an object accrue to all multi-modal imaging systems, such as, for example, but not limited to, a PET-CT imaging system.

In the various embodiments, different imaging modalities may be used. For example, in computed tomography (CT) imaging system configurations, an X-ray source projects a fan-shaped beam that is collimated to lie within an X-Y plane of a Cartesian coordinate system and generally referred to as an "imaging plane." The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements (e.g., projection data) from the detector array at one gantry angle is referred to as a "view." A "scan" of the object comprises a set of views made at different gantry angles, or view angles, during one revolution of the X-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a cathode ray tube or other type of image display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed. Alternatively, an "axial" scan (e.g., a single rotation without the table moving) may be performed. Optionally, a "cine" scan (e.g., as the gantry spins during multiple cycles at the same location as multiple images are acquired during each turn of the gantry) may be performed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a two dimensional slice taken through the object.

To further reduce the total acquisition time, multi-slice CT may be used. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

At least some CT systems are configured to also perform Positron Emission Tomography (PET) and are referred to as PET-CT systems. PET scanners incorporate a process similar to that found in CT, in that a map of the object attenuation can be generated. A method to perform this attenuation measurement includes the use of rotating rod sources containing positron-emitting radionuclides. The rods rotate outside the patient bore, but inside the diameter of the PET detector ring. Annihilation events occurring in the rods can send one photon into a near-side detector while the pair photon traverses the object of interest in a manner similar to the CT X-ray. The data found from this method contains essentially the same image information as that found from the CT method except for the statistical quality of the resultant data. In the rotating rod case, the statistical quality is orders of magnitude inferior to most common CT scans. For the PET purpose, data acquired in this manner is used to correct for the attenuation seen in the object by the 511 keV photons from the annihilation events as described in more detail below and which is often the most substantial correction performed on the PET data.

Positrons are positively charged electrons (anti-electrons) that are emitted by radionuclides that have been prepared using a cyclotron or another device. The radionuclides most often employed in diagnostic imaging are fluorine-18 ($^{18}F$), carbon-11 ($^{11}C$), nitrogen-13 ($^{13}N$), and oxygen-15 ($^{15}O$), among others. Radionuclides are employed as radioactive tracers called "radiopharmaceuticals" that are incorporated into substances such as glucose or carbon dioxide.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism and protein synthesis. Hereinafter, in the interest of simplifying this explanation, an organ to be imaged, including a vessel, will be referred to generally as an "organ of interest" and various embodiments of the invention will be described with respect to a hypothetical organ of interest.

After the radiopharmaceutical becomes concentrated within an organ of interest and while the radionuclides decay, the radionuclides emit positrons. The positrons travel a very short distance before they encounter an electron and, when the positron encounters an electron, the positron is annihilated and converted into two photons or gamma rays. This annihilation event is characterized by two features that are pertinent to medical imaging and particularly to medical imaging using PET. First, each gamma ray has an energy of approximately 511 keV upon annihilation. Second, the two gamma rays are directed in nearly opposite directions (e.g., 180 degrees apart).

In PET imaging, if the general locations of annihilations can be identified in three dimensions, a three dimensional image of radiopharmaceutical concentration in an organ of interest can be reconstructed for observation. To detect annihilation locations, a PET camera is employed. An exemplary PET camera includes a plurality of detectors and a processor which, among other things, includes coincidence detection circuitry as described in more detail below.

The coincidence circuitry identifies essentially simultaneous pulse pairs, which correspond to detectors that are essentially on opposite sides of the imaging area. Thus, a simultaneous pulse pair indicates that an annihilation has occurred along a straight line between an associated pair of detectors. Over an acquisition period of a few minutes, millions of annihilations are recorded, where each annihilation is uniquely associated with a detector pair. After an event acquisition period, recorded annihilation data can be used by any of several different well known image reconstruction methods to reconstruct a three dimensional image of radionuclide concentration in the organ of interest.

FIG. 1 is a block diagram of a medical imaging system 100 formed in accordance with an exemplary embodiment of the present invention. The system found in accordance with an embodiment of the present invention may be any emission-type computed tomography imaging system including, but not limited to, a single Positron Emission Tomography (PET) scanner, a dual PET/CT scanner, a single nuclear (photon emission) computed tomography (SPECT) scanner, or a dual SPECT/CT scanner, among others.

The medical imaging system 100, such as, for example, a PET/CT system, includes a gantry 102, a patient table 104, and a computer system 106. Gantry 102 provides mechanical support for mounting devices such as, for example, detectors, scanners and transmitters that are useful for scanning a patient 107. Gantry 102 houses imaging devices such as, for example, PET detectors. The PET system may be a stationary annular detector and, optionally, may include a pin source for PET.

The imaging devices on gantry 102 acquire image data by scanning a patient 107 lying on patient table 104. Moving patient table 104 enables the scanning of various parts of the patient 107. Patient table 104 lies along the axis of gantry 102, which is known as a viewing area axis (as shown in FIG. 1) and can be moved along this viewing area axis. Patient table 104 can be positioned at various axial positions along the viewed area axis. In an embodiment of the invention, gantry 102 includes a plurality of detectors that are fixed and spaced on gantry 102 positioned facing radially inward toward the viewing area axis. In accordance with an embodiment of the invention, gantry 102 includes a plurality of detectors that can rotate about the viewing area axis. Further, the table and/or gantry can move along the axis, enabling the scanning of various parts of the patient at different axial positions (e.g., superior to inferior). For CT imaging, for example, a rotating detector and a source, moving table, and optionally including, a stationary detector ring for CT may be provided.

In an embodiment of the invention, computer system 106 controls, for example, the positioning of patient table 104. Specifically, computer system 106 is programmed to position patient table 104 at a plurality of axial positions along the viewing area axis. Positioning table 104 enables the scanning of different axial positions of the patient 107. Computer system 106 may further be programmed to keep a track of the position of patient table 104. Computer system 106 is also programmed to receive image data collected during scanning. In accordance with various embodiments of the invention, computer system 106 includes a processor, such as a Linux® based or a Windows® based PC, for user interface and custom array processor boards for image reconstruction.

A scan time may also be fixed or predetermined, for example, by a user or computer system 106. In the case where the user predetermines the scan time, computer system 106 may receive an indication of the scan time. This may help computer system 106 to control the scanning. In addition to providing the scan time, the user may also provide computer system 106, an indication of the location of a volume of interest. The volume of interest is that part of the patient that is to be scanned (e.g., an organ, a tissue, a specific region of interest). In one embodiment, the volume of interest may be selected by a user and input to computer system 106. In various embodiments of the invention, computer system 106 controls medical imaging system 100 to acquire the scan data and determine a volume of interest based on the transmission data. In an embodiment of the invention, computer system 106 controls medical imaging system 100 to perform, for example, at least one of a CT scan, a PET transmission scan, and a CT scout scan to acquire the transmission data. In various embodiments of the invention, computer system 106 is programmed to automatically move a volume of interest from a first position corresponding to a frame that includes a first axial periphery of the volume of interest to a second position corresponding to a frame that includes a second axial periphery of the volume of interest. In an embodiment of the invention, computer system 106 moves the volume of interest in response to a user input. In another embodiment of the invention, computer system 106 automatically moves the volume of interest based on the transmission data.

In addition, medical imaging system 100 may include a transmission source (not shown). The transmission source is located such that the particles emitted by the transmission source pass through the volume of interest of the patient 107. The signals may be attenuated when the signals pass through a volume of interest of the patient 107. Hence, the detectors may collect data that is attenuated as the particles pass through the patient 107. The transmission source is, thus, used to acquire attenuation data relative to the patient 107. In accordance with an embodiment of the invention, computer system 106 may be programmed to generate an attenuation correction relative to the patient 107 using the transmission source. Computer system 106 may further be programmed to determine the scan time for a frame of image data based on the attenuation data. Each frame of image data is a part of image data that corresponds to an axial position of the patient 107. The frames acquired may be at least one of a spatial frame of image data, a temporal frame of image data, or a combination thereof. Moving patient table 104 along the viewing area axis enables the scanning of different axial positions of the patient 107. In various embodiments of the invention, computer system 106 is programmed to modulate the time spent at a particular location of patient table 104. This enables a user of medical imaging system 100 to increase or decrease the acquisition time of a particular region of the body.

The attenuation data is received by computer system 106. Computer system 106 may use the received attenuation data, for example, to determine the scan time for each frame of image data.

Various processors, sorters, and databases are used to acquire and manipulate scan data, including, for example, emission and transmission data. The processors, sorters and databases of FIG. 1 include acquisition circuitry 125, an acquisition processor 130, a transmission data database 171, an emission database 172, and an image reconstruction processor 174. In various embodiments of the invention, acquisition processor 130 is programmed to acquire emission data in the list mode and sinogram mode, as described in more detail below, and generate the image based on the emission data acquired in the list mode, the emission data acquired in the sinogram mode and the time-of-flight (TOF) information of the emission data. Other computing components may be included with the system, which have been omitted here in the interest of simplification.

In one embodiment, sorter 169 provides the time, location, and energy data to PET processor 170. Processor 170 generally uses the received data to identify pairs of data, also known as coincidence pairs, coincident pair lines and lines of response, corresponding to annihilation events that occurred inside the region of interest. After acquisition processor 130 identifies an annihilation event, the acquisition processor 130 updates data in emission database 172 to store information relating to the annihilation event.

After the acquisition session has been completed, and complete sets of transmission and emission data have been stored in databases 171 and 172, respectively, the image reconstruction processor 174 accesses the data in databases 171 and 172. The image reconstruction processor 174 uses the accessed data to generate images that may be requested by a system operator. The operator can use computer system 106 to select image types and views. For instance computer system 106 may be configured to output a graph of gross patient motion. Alternatively, computer system 106 may provide the graph of gross patient motion to at least one of a personal digital assistant and a remote computer monitor that is connected via at least one of a LAN connection, an Internet connection, a hardwired landline connection, and a satellite connection to an axis point in a remote office.

Figure 2:
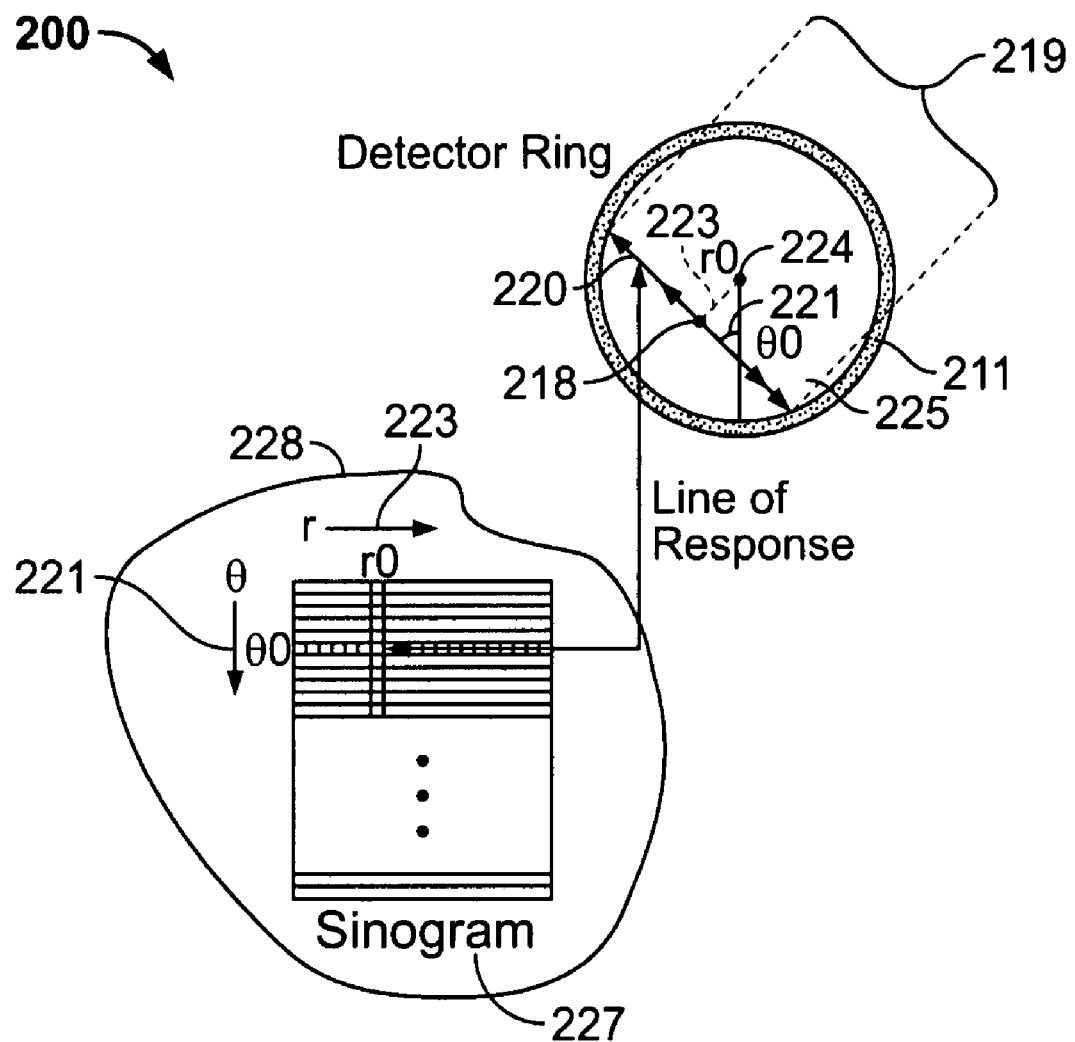
FIG. 2 is a perspective view of a detector ring and an illustration of the construction of a sinogram formed in accordance with an embodiment of the present invention.

FIG. 2 is a perspective view 200 of a detector ring 211 and an illustration 228 of the construction of a sinogram 227 formed in accordance with an embodiment of the present invention. In positron emission tomography (PET), sorter 169 (shown in FIG. 1) receives a coincidence event pair 219 of an annihilation event 218 and identifies a corresponding line of response 220. Each line of response 220 may be identified by an angle ($\theta$) 221 and a distance (r) 223 from a center 224 of the field of view 225. The array of the responses 220 is known as a sinogram 227.

System 100 has multiple rings 211 of detectors covering, for example, 15-25 centimeters in the axial direction. Detectors typically include radiation sensors with sufficiently high density and timing resolution. The high timing resolution may be required to discriminate between at least two positions along the line of response 220 joining two such detectors. The photons are emitted in opposite direction along the line of response 220 and are simultaneously detected by detectors placed on the line of response 220.

PET data may be acquired in either a 2-dimensional or a 3-dimensional mode. In the 2-dimensional acquisition mode, lines of responses 220 occurring in the same ring 211 and/or adjacent rings 211 are accepted. In the 3-dimensional mode, any line of response 220 occurring between any pair of detector rings 211 is acquired. In the two-dimensional mode, data planes are formed, called direct planes, by combining events where both photons are detected within the same ring 211 or where the ring difference is even (e.g., 0, 2, 4, . . . ) while cross-planes are formed from events detected with an odd ring difference (e.g., 1, 3, 5 . . . ).

Although the specific embodiment mentioned above refers to third generation CT system and a PET imaging system, the methods described herein equally apply to a fourth generation CT systems (e.g., stationary detector and a rotating X-ray source), fifth generation CT systems (e.g., stationary detector and X-ray source), or other PET-only or nuclear systems (e.g., MRI) wherein imaging is provided.

Figure 3:
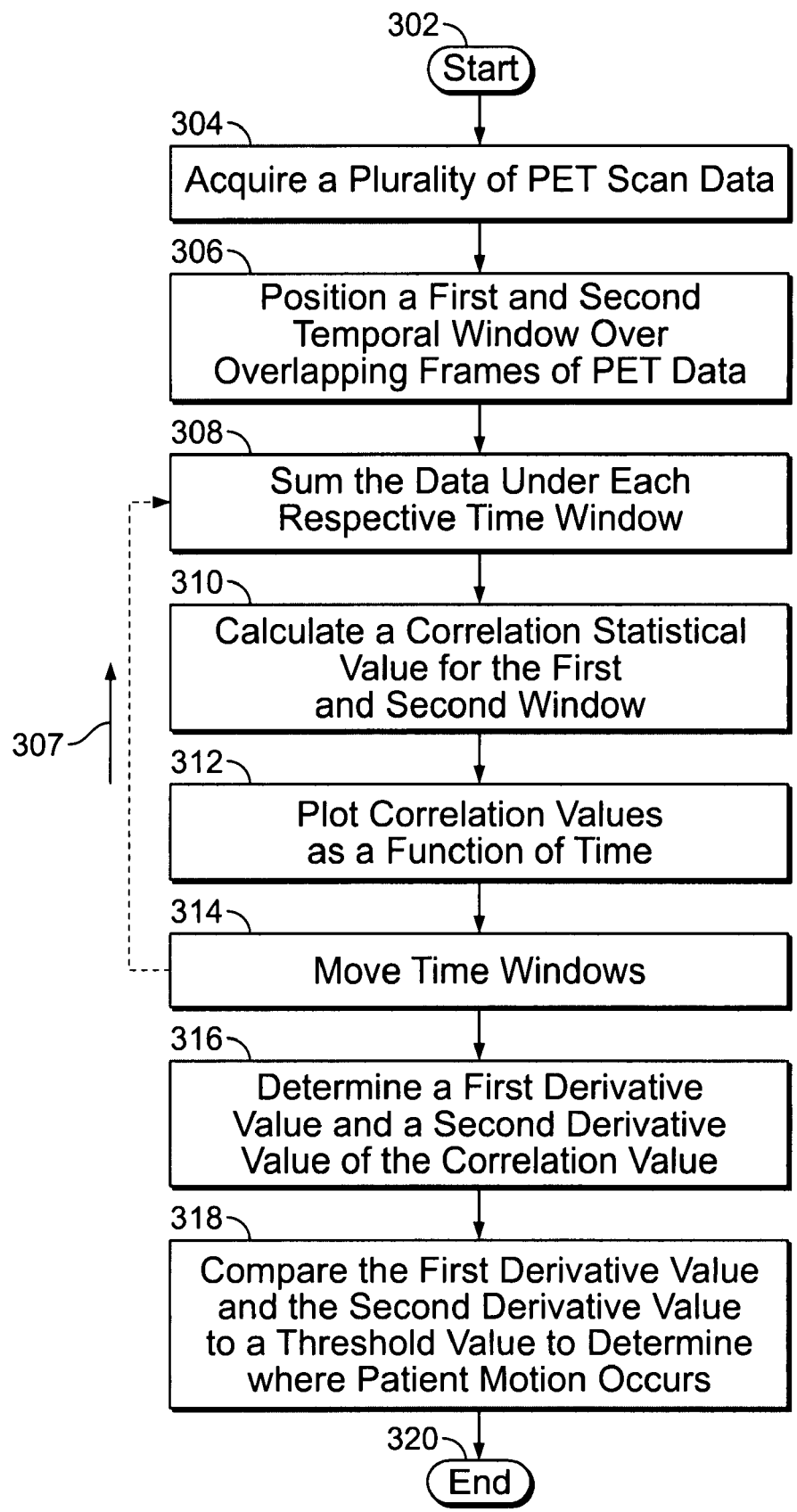
FIG. 3 is a flowchart illustrating a method for automatically determining gross patient movement in PET-CT in accordance with an embodiment of the present invention.

FIG. 3 illustrates a flow chart of a method 300 of automatically determining gross patient movement in a PET/CT imaging system 100 in accordance with an embodiment of the present invention. This embodiment represents a 'step-and-shoot' type PET scan, whereby the process described in method 300 may be repeated at each step. At 302, the process begins.

At 304, the imaging system 100 acquires a plurality of PET scan data from a patient 107. The data may be image data. Alternatively, the data may be sinogram data. Optionally, the data may be non-attenuated whole-body fluorodeoxyglucose (FDG) images. The data may be configured into datasets of images that are organized in a temporal sequence. A group of datasets may overlap one another.

At 306, a first window and a second window are placed over a set of overlapping (in space) frames of PET data. The frames of PET data may be at least a spatial frame of image data or a temporal frame of image data, or a combination thereof. Data in these time windows may be constructed from one or many slices within the frame. The time windows may further be adjacent in time or separated by a pre-defined time. The windows have a pre-defined width (e.g., in seconds), which may be user selected. Alternatively, the width of the windows may be automatically selected based on the statistical quality of the PET data. Each window has an associated time location. As time progresses, each window moves over at least one image frame, (e.g., as a rolling time window, from start of frame to end of frame). Thus, each window contains at least one image of the previous dataset. At 308, the image or sinogram data underneath each time window is summed.

At 310, data within the two time windows are compared by using a statistical calculation. In one embodiment, the statistical calculation that is performed is a statistical data-element by data-element correlation of the two time windows according to Equation 1, as described below. In an exemplary embodiment, a set of correlation values may be generated for all the acquired datasets, as pairs of datasets are acquired between adjacent datasets. Thus, a plurality of correlation values may be generated. The plurality of correlation values may be stored in a memory of processor 130, stored in a database (for example, such as transmission database 171 or emission database 172), or stored any other memory or database connected to system 100. A change in the correlation value across a temporal boundary may indicate where the motion occurred. At 312, the correlation values as a function of the time location are plotted and at 314, the time windows are moved. The method 300 flow follows the dashed line at 307 back to step 308 to repeat the method over the duration of the frame.

At 316, first and second derivatives of the correlation values as a function of time are determined using any known process. A change in the derivative of the time-to-time correlation is representative of gross patient motion (e.g., arm motion, leg motion, head motion, upper body motion, lower body motion, and the like). A change in correlation is indicative of patient motion because if the patient were still, the activity contained at a certain location at time 0-5 s would still be in the same location at time 5-10 s, and hence the data element correlation would be high. For instance, if the arm moved at 5 s, then the data collected in the 0-5 s time window would not be expected to be spatially correlated to data in a 5-10 s time window. The sensitivity of the correlation value (e.g., change in time-to-time correlation of the data) may be amplified by determining the first and second derivatives of the correlation value and monitoring the first and second derivatives as a function of time (see 250, 251 in FIG. 5).

At 318, the first derivative value and the second derivative value may be compared with a threshold value. A correlation value that exceeds the threshold value indicates where gross patient motion occurs. The method 300 may be performed during a scan acquisition, after a scan acquisition, and during a reconstruction. While a scan is in progress, an operator may measure and track over a period of time a quantity of occurrences where the derivative function exceeds a threshold. As the number of occurrences increase during the scan, the data can be assessed to determine a proper action to take, such as, but not limited to, repeating the scan, repositioning a patient, addressing patient comfort, and lengthening scan time. This action may be performed automatically or may require user initiation or approval. At 320, the user may select to repeat process 300 or terminate the process.

A further embodiment of the above described process, a histogram (not shown) of spatial correlation values calculated over time (and possible first and second derivative values) can be formed and analyzed for patterns indicating local-region motion (such as may be seen for respiration) as compared to gross (whole-body-shift) motion.

Figure 4:
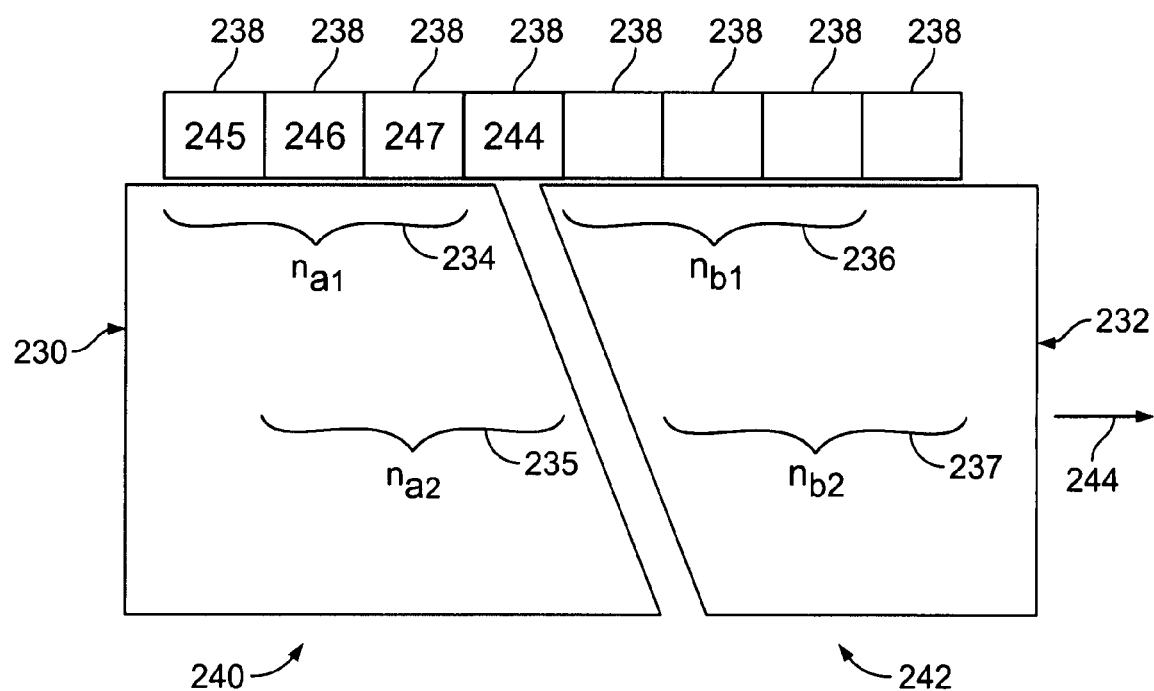
FIG. 4 is an illustration of two regions utilized in accordance with an embodiment of the present invention.

FIG. 4 illustrates two temporal regions or "neighborhoods" in accordance with an embodiment of the present invention. A "neighborhood" 230 and 232 is defined by groups of overlapping datasets 234-237. The datasets 234-237 provide a set of summed images 238. Each neighborhood 230 and 232 of images 238 may be averaged to generate a single slice. The datasets 234-237 may overlap one another, as well as be in a temporal sequence. Two windows 240 and 242 are shown (e.g., $n_a$ and $n_b$). Each temporal window may be separated by at least one time element 244 of a pre-defined width. Alternatively more than one time element may be used to separate the windows, or no separation may be used. The windows 240 and 242 may have a pre-defined width (e.g., in seconds), which may be user selected. Alternatively, the width of the windows 240 and 242 may be automatically selected based on the statistical quality of the PET data. Each window has an associated time interval. For instance, data sets 234 and 236 are located at a first time (e.g., noted as $na_1$ and $nb_1$), and data sets 235 and 237 are located at a second time (e.g., noted as $na_2$ and $nb_2$). As time progresses, each window 240 and 242 moves toward the right as indicated by arrow 244 and a new overlapping dataset is created. The new dataset may contain images 238 of the previous dataset. For instance, dataset 234 includes images 245, 246, and 247. When window 240 moves to the right, the dataset 235 is created, which includes images 246 and 247 from the previous dataset 234. Typically, such movement by windows 240 and 242 is called a rolling time window.

A plurality of correlation values are generated in accordance with the following equation:

$$Correl(a, b) = \frac{1}{(n-1)} \frac{\sum (a_i - \overline{a})(b_i - \overline{b})}{s_a s_b} \quad \text{Eqn. 1}$$

where and b represent elements in a dataset (e.g., [r, θ] for a sinogram or [x,y] pixel value for an image); n is the number of elements in a dataset; $a_i$ is an $i^{th}$ element of dataset a; $b_i$ is an $i^{th}$ element of dataset b; $\overline{a}$ is an average of all the elements in dataset a; $\overline{b}$ is an average of all the elements in dataset b; $s_a$ is a standard deviation of the elements in dataset a; and $s_b$ is a standard deviation of the elements in dataset b.

Adjacent groups of datasets may be correlated using Equation 1 above. More specifically, Equation 1 may use a first dataset and a second subsequent dataset to generate the correlation value. For example, datasets 234 and 236 may be correlated. A correlation value may then be generated using the second dataset and a third subsequent dataset. For instance, datasets 235 and 237 may be correlated. In an exemplary embodiment, a correlation value may be generated for all the acquired datasets, as pairs of datasets are acquired between adjacent datasets. Thus, a plurality of correlation values may be generated. The plurality of correlation values may be stored in a memory of processor 130, stored in a database (e.g., transmission database 171 or emission database 172), or stored any other memory or database connected to system 100.

Figure 5:
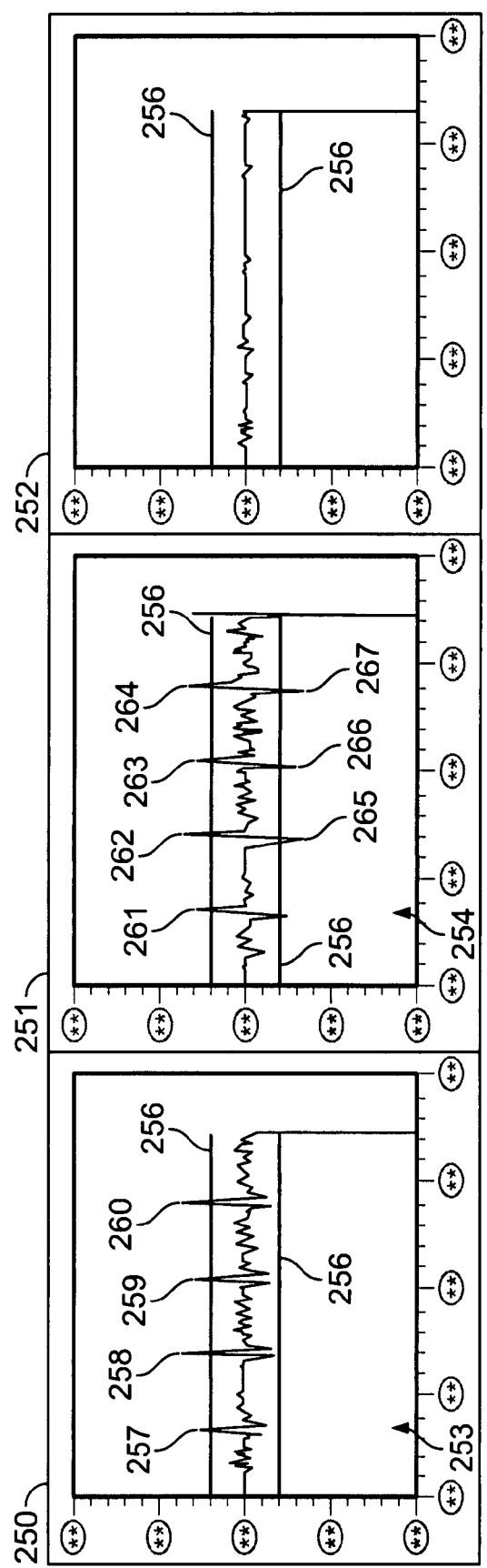
FIG. 5 depicts plots of various derivatives based on a correlation function utilized in accordance with an embodiment of the present invention.

A shift in a correlation value may indicate that gross patient motion exists. For example, datasets of the summed images 247 defined by the temporally rolling windows 240 and 242 may be compared by determining a correlation value using equation 1. A change in the correlation value across a temporal boundary may indicate where the motion occurred. FIG. 5 illustrates three plots 250, 251, and 252 that depict gross patient motion. Plot 250 shows a plot of a first derivative 253 of the correlation of a plurality of a datasets. The x-axis in plots 250, 251, and 252 represents time, while the y-axis is unit-less and is scaled for relative comparison. Plot 251 shows a plot of a second derivative 254 of the correlation of a plurality of a datasets. Plot 252 shows a plot of correlation values where no significant gross motion occurs. An abrupt shift in the correlation value may represent gross patient motion. A shift or change in the correlation function may be amplified by taking a first derivative 250 or a second derivative 251 of the correlation function. As indicated in FIG. 5, solid lines represent a threshold value 256. A correlation value that exceeds the threshold value 256 (e.g., 257-266) indicates where gross patient motion occurs. The threshold value for user intervention may be learned over time from experience or may be determine from a database of correlation plots using the described invention where motion is deemed to be acceptable versus problematic. It is also noted that the systems and methods for assessing gross patient motion can be implemented in other imaging modalities such as, for instance, positron emission tomography (PET), single photon emission computed tomography (SPECT), computed tomography (CT), and magnetic resonance imaging (MRI) systems.

The various embodiments or components thereof may be implemented as part of a computer system. The computer system may include a computer, an input device, a display unit, and an interface, for example, for accessing the Internet. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

In various embodiments of the invention, the method of creating a CT attenuation correction image as described herein or any of its components may be embodied in the form of a processing machine. Typical examples of a processing machine include a general-purpose computer, a programmed microprocessor, a digital signal processor (DSP), a microcontroller, a peripheral integrated circuit element, and other devices or arrangements of devices, which are capable of implementing the steps that constitute the methods described herein.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer."

The processing machine executes a set of instructions (e.g., corresponding to the method steps described herein) that are stored in one or more storage elements (also referred to as computer usable medium). The storage element may be in the form of a database or a physical memory element present in the processing machine. The storage elements may also hold data or other information as desired or needed. The physical memory can be, for example, but not limited to, an electronic, magnetic, optical, electromagnetic, infrared, or semiconductor system, apparatus, device, or propagation medium. More specific examples of the physical memory include, but are not limited to, the following: a random access memory (RAM) a read-only memory (ROM), an erasable programmable read-only memory (EPROM or Flash memory), a Hard Disc Drive (HDD) and a compact disc read-only memory (CDROM).

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

A technical effect of the various embodiments is to use a diagnostic imaging system, such as a PET-CT system, to acquire a plurality of frames of image data, position a first time window and a second time window over overlapping frames of image data, calculate a statistical correlation value based on the first time window and the second time window, and determine gross patient motion by comparing a first derivative of the statistical correlation value to a threshold value.

In various embodiments of the invention, the method of creating an ultrasound medical image can be implemented in software, hardware, or a combination thereof. The methods provided by various embodiments of the present invention, for example, can be implemented in software by using standard programming languages such as, for example, C, C++, Java, and the like.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus limiting as to the types of memory usable for storage of a computer program.

The analysis described above may be performed on several different data sets. Calculations may be performed on individual slices or rings or detectors, groups of slices, all slices, or a select line of responses, specific r and θ ranges, and the like. The analyzed data set may be modified to focus on the motion of specific organs or structures. The physiological structure may include a biological organ, for example, the stomach, heart, lung or liver; a biological structure, for example, the diaphragm, chest wall, rib cage, rib, spine, sternum or pelvis; or a foreign object fiducial marker, for example, a marker placed for the purpose of gating; a tumor, or a lesion or sore, for example, a bone compression fracture.

Thus, what is provided is a better method and apparatus for medical imaging using a PET-CT to determine gross patient movement, including both voluntary motion and involuntary motion.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method of automatically detecting gross patient motion using a diagnostic medical imaging system, said method comprising:
   acquiring a plurality of overlapping frames of image data;
   positioning a first time window and a second time window over a first portion of the data, the first time window being separated from the second time window by a predetermined time;
   calculating a first statistical correlation value based on the first portion of data included in the first time window and the second time;
   repositioning the first time window and the second time window over a second portion of the data, the second portion of data at least partially overlapping the first portion of data;
   calculating a second statistical correlation value based on the second portion of data included in the first time window and the second time window; and
   determining patient motion by comparing a first derivative of the first and second statistical correlation values to a threshold value.

2. The method according to claim 1, further comprising summing the plurality of image data within each time window.

3. The method according to claim 1, wherein the predetermined time is a non-zero time such that the first time window does not overlap with the second time window.

4. The method according to claim 1, wherein determining patient motion comprises calculating a second derivative of at least one of the first and second statistical correlation values.

5. The method according to claim 1, wherein determining patient motion comprises performing at least one of a lengthening of a scan time, re-scanning, and determining a quality level.

6. The method according to claim 1, wherein acquiring a plurality of frames of image data comprises acquiring at least one of sinogram data, list mode data, attenuation-corrected PET data, non-attenuation corrected PET data, where the frames are at least one of a spatial frame and a temporal frame.

7. The method according to claim 1, wherein determining patient motion is determined at least as soon as a frame of PET data is acquired and during acquisition of the PET data.

8. The method according to claim 1, wherein the motion comprises gross motion including at least one of a voluntary motion and an involuntary motion.

9. The method according to claim 1, wherein the statistical correlation value is determined by:

$$Correl(a,b) = \frac{1}{(n-1)} \frac{\sum (a_i - \bar{a})(b_i - \bar{b})}{s_a s_b}$$

wherein, a and b represent elements in a dataset; n is the number of elements in a dataset; $a^i$ is an $i^{th}$ element of dataset a; $b_i$ is an $i^{th}$ element of dataset b; $\bar{a}$ is an average of all the elements in dataset a; $\bar{b}$ is an average of all the elements in dataset b; $s_a$ is a standard deviation of the elements in dataset a; and $s_b$ is a standard deviation of the elements in dataset b.

10. The method according to claim 1, wherein the data comprises a plurality of frames of data and wherein the first and second windows form a rolling window, the method further comprising automatically moving the rolling window temporally over the plurality of frames of image data to a plurality of window positions to acquire a statistical correlation value for each window position.

11. The method according to claim 1, wherein the data comprises a plurality of overlapping images acquired from a scan start time to a scan end time, said method further comprising automatically moving the first and second windows to a plurality of window positions temporally located between the scan start time and the scan end time to generate a statistical correlation value for each window position.

12. The method according to claim 1, wherein the first time window is adjacent in time to the second time window.

13. The method accordingly to claim 1, wherein the first and second time windows each have a predetermined time width.

14. A diagnostic medical imaging system, comprising:
a scanner to acquire spatial frames of image data from a patient;
a processor including a non-transitory computer readable medium being programmed to:
position a first time window and a second time window over a first portion of data, the first time window being separated from the second time window by a predetermined distance;
calculate a first statistical correlation value based on the first portion of data included in the first time window and the second time window;
reposition the first time window and the second time window over a second portion of the data, the second portion of data at least partially overlapping the first portion of data;
calculate a second statistical correlation value based on the second portion of data included in the first time window and the second time window; and
compare a first derivative of the first and second statistical correlation values to a threshold value; and
a display for outputting a graph of gross patient motion.

15. The system according to claim 14, wherein the image data comprises at least one of sinogram data, list mode data, and non-attenuation corrected positron emission tomography (PET) data.

16. The system according to claim 14, wherein overlapping frames of image data comprise a sum of a plurality of image data within each time window.

17. The system according to claim 14, wherein the first window and second window are separated by at least a single image frame.

18. The system according to claim 14, further comprising a connection to a network to transmit at least one of image data, the statistical correlation values, the threshold, and a comparison of the statistical correlation value and the threshold to a remote computer.

19. The system according to claim 14, wherein the display if further configured to output a graph of gross patient motion to at least one of a personal digital assistant and a remote computer monitor connected via at least one of a LAN connection, an internet connection, a hardwired land-line connection, and a satellite connection to an axis point in a remote office.

20. The system according to claim 14, wherein the processor is further configured to calculate a second derivative of the statistical correlation value, wherein the second derivative determines when the correlation value is at least one of a maximum and a minimum.

21. The system according to claim 14, wherein the first derivative of the statistical correlation value comprises a change in the correlation value across a temporal boundary, wherein the change indicates where the motion occurred.

22. The system according to claim 14, wherein the statistical correlation value is determined by:

$$Correl(a,b) = \frac{1}{(n-1)} \frac{\sum (a_i - \bar{a})(b_i - \bar{b})}{s_a s_b}$$

wherein, a and b represent elements in a dataset; n is the number of elements in a dataset; $a_i$ is an element of dataset a; $b_i$ is an $i^{th}$ element of dataset b; $\bar{a}$ is an average of all the elements in dataset a; $\bar{b}$ is an average of all the elements in dataset b; $s_a$ is a standard deviation of the elements in dataset a; and $s_b$ is a standard deviation of the elements in dataset b.

23. A non-transitory computer readable medium for use in a diagnostic medical imaging system having a scanner to acquire frames of image data from a patient and a processor, the computer readable medium including instructions that instructs the diagnostic medical imaging system to:
acquire Positron Emission Tomography (PET) image data from an object;
position a first time window and a second time window over a first portion of the overlapping frames of the image data;
calculate a first statistical correlation value based on the first portion of data included in the first time window and the second time window;
reposition the first time window and the second time window over a second portion of the data, the second portion of data at least partially overlapping the first portion of data;

calculate a second statistical correlation value based on the second portion of data included in the first time window and the second time window;

compare a first derivative of the first and second statistical correlation values to a threshold value; and v) display a graph representing an indicator of gross motion of the patient.

* * * * *

UNITED STATES PATENT AND TRADEMARK OFFICE
CERTIFICATE OF CORRECTION

| | | |
|---|---|---|
| PATENT NO. | : 8,107,695 B2 | |
| APPLICATION NO. | : 11/823231 | |
| DATED | : January 31, 2012 | |
| INVENTOR(S) | : Wollenweber | |

It is certified that error appears in the above-identified patent and that said Letters Patent is hereby corrected as shown below:

On Page 2, in Field (56), under "OTHER PUBLICATIONS", in Column 2, Line 4, delete ""Attentuation" and insert -- "Attenuation --, therefor.

In Column 9, Line 61, delete "where" and insert -- where a --, therefor.

In Column 12, Line 51, in Claim 1, delete "time;" and insert -- time window; --, therefor.

In Column 13, Line 28, in Claim 9, delete "$a^i$" and insert -- $a_i$ --, therefor.

In Column 13, Line 49, in Claim 13, delete "accordingly" and insert -- according --, therefor.

In Column 14, Line 46, in Claim 22, delete "an" and insert -- an $i^{th}$ --, therefor.

In Column 16, Line 1, in Claim 23, delete "v) display" and insert -- display --, therefor.

Signed and Sealed this
Eighteenth Day of September, 2012

David J. Kappos
*Director of the United States Patent and Trademark Office*